(12) United States Patent
Canham et al.

(10) Patent No.: US 8,318,194 B2
(45) Date of Patent: *Nov. 27, 2012

(54) IMPLANTS FOR ADMINISTERING SUBSTANCES AND METHODS OF PRODUCING MESOPOROUS IMPLANTS

(75) Inventors: Leigh T. Canham, Malvern (GB); Christopher P. Barrett, Malvern (GB); Andrew P. Bowditch, Salisbury (GB); Timothy I. Cox, Malvern (GB); Peter J. Wright, Malvern (GB)

(73) Assignee: PSIMedica Limited, Malvern (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/801,825

(22) Filed: Jun. 28, 2010

(65) Prior Publication Data

US 2011/0052659 A1    Mar. 3, 2011

Related U.S. Application Data

(63) Continuation of application No. 09/647,599, filed as application No. PCT/GB99/01185 on Apr. 16, 1999, now Pat. No. 7,763,277.

(30) Foreign Application Priority Data

Apr. 17, 1998   (GB) .................................. 9808052.6

(51) Int. Cl.
    *A61F 2/02* (2006.01)
(52) U.S. Cl. ...................................................... 424/426
(58) Field of Classification Search .................. None
    See application file for complete search history.

(56) References Cited

U.S. PATENT DOCUMENTS

| | | |
|---|---|---|
| 3,832,458 A | 8/1974 | Merrill |
| 3,919,060 A | 11/1975 | Pogge et al. |
| 3,919,723 A | 11/1975 | Heimke et al. |
| 4,036,979 A | 7/1977 | Asato |
| 4,608,048 A | 8/1986 | Cortese et al. |
| 4,772,203 A | 9/1988 | Scheunemann |
| 4,793,825 A | 12/1988 | Benjamin et al. |

(Continued)

FOREIGN PATENT DOCUMENTS

EP   0 178 769 B1   5/1989

(Continued)

OTHER PUBLICATIONS

Canham, "Porous Silicon as a Therapeutic Biomaterial", 1st Annual International IEEE-EMBS Special Topic Conference on Microtechnologies in medicine & Biology, Oct. 12-14, 2000, Lyon, France.*

(Continued)

*Primary Examiner* — Carlos Azpuru
(74) *Attorney, Agent, or Firm* — Ropes & Gray LLP; David P. Halstead; David P. Pleynet

(57) ABSTRACT

A porous silicon implant impregnated with a beneficial substance, such as a micromineral required for healthy physiology, is implanted subcutaneously and is entirely corroded away over the following months/year to release the micromineral in a controlled manner. In a second embodiment the implant may have a large number of holes which contain beneficial substance and which are closed by bio-errordable doors of different thickness so as to stagger the release of the beneficial substance over time as the doors are breached.

41 Claims, 9 Drawing Sheets

U.S. PATENT DOCUMENTS

| | | |
|---|---|---|
| 5,591,453 A | 1/1997 | Ducheyne et al. |
| 5,797,898 A | 8/1998 | Santini, Jr. et al. |
| 5,874,109 A | 2/1999 | Ducheyne et al. |
| 5,922,299 A | 7/1999 | Bruinsma et al. |
| 6,060,036 A | 5/2000 | Armini |
| 6,086,908 A | 7/2000 | Gopferich |
| 6,322,895 B1 | 11/2001 | Canham |
| 6,666,214 B2 | 12/2003 | Canham |
| 6,696,258 B1 | 2/2004 | Wei et al. |
| 2002/0034646 A1 | 3/2002 | Canham |

FOREIGN PATENT DOCUMENTS

| | | |
|---|---|---|
| JP | 59-101145 | 6/1984 |
| JP | 59-131346 | 7/1984 |
| WO | WO 90/11070 | 10/1990 |
| WO | WO 92/05777 | 4/1992 |
| WO | WO 94/21314 | 9/1994 |
| WO | 97/06101 | 2/1997 |
| WO | 97/32570 | 9/1997 |
| WO | WO 99/39746 | 8/1999 |

OTHER PUBLICATIONS

Vinegoni et al, "Porous silicon microcavities", Oct. 2000, "Silicon-Based Materials and Devices", vol. 2: "Properties and Devices", Hari Singh Nalwa, ISBN: 0125139195; Publisher: Academic Press.

*New Scientist*, 1997, vol. 153, No. 2075, pp. 36-39.

Canham, "Porous Silicon as a Therapeutic Biomaterial", $1^{st}$ Annual International IEEE-EMBS Special topic Conference on Microtechnologies in Medicine & Biology, Oct. 12-14, 2000, Lyon, France.

\* cited by examiner

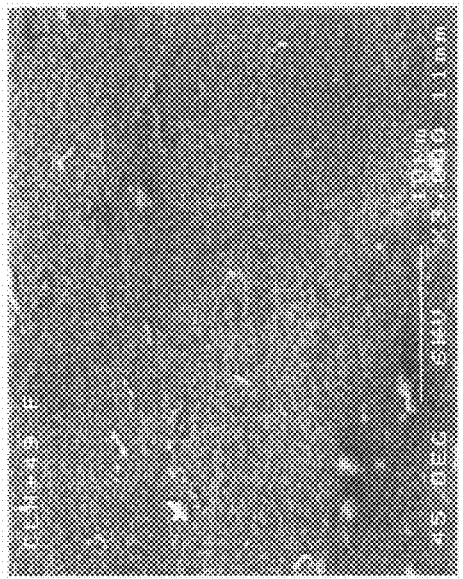
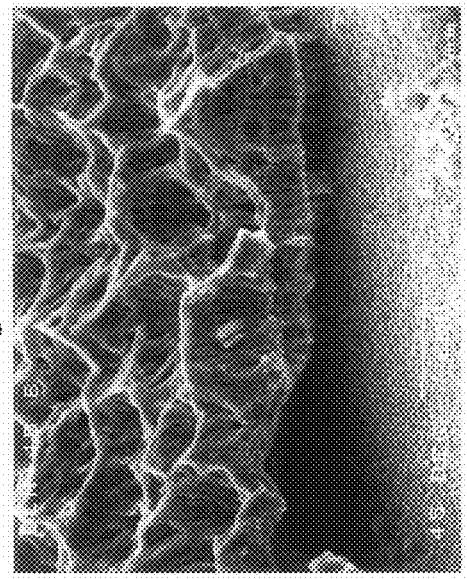
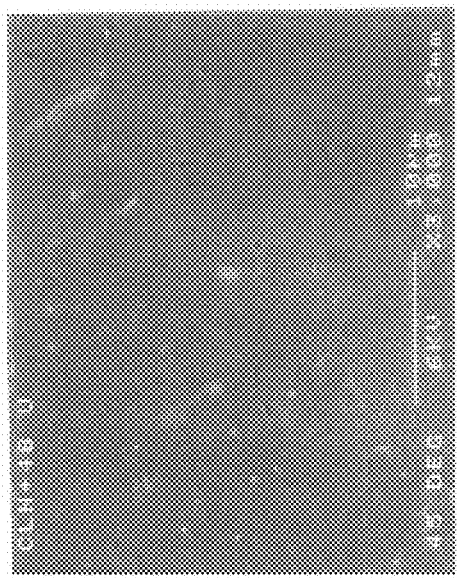
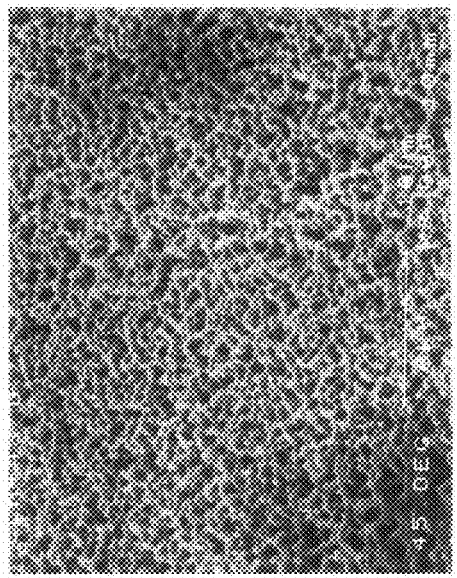

Fig. 5.

M Practical Problems in Man
? Essentiality Questioned By Some. (3 Li, 82 Pb)

☐ Trace Elements
▓ Essential
▨ Practical Problems: Deficiency
▧ Practical Problems: Excess

| 1 H | | | | | | | | | | | | | | | | | 2 He |
|---|---|---|---|---|---|---|---|---|---|---|---|---|---|---|---|---|---|
| 3 Li ? | 4 Be | | | | | | | | | | | 5 B | 6 C | 7 N | 8 O | 9 F M | 10 Ne |
| 11 Na | 12 Mg | | | | | | | | | | | 13 Al | 14 Si | 15 P | 16 S | 17 Cl | 18 Ar |
| 19 K | 20 Ca | 21 Sc | 22 Ti | 23 V | 24 Cr M | 25 Mn | 26 Fe M | 27 Co | 28 Ni | 29 Cu M | 30 Zn M | 31 Ga | 32 Ge | 33 As | 34 Se M | 35 Br | 36 Kr |
| 37 Rb | 38 Sr | 39 Y | 40 Zr | 41 Nb | 42 Mo M | 43 Tc | 44 Ru | 45 Rh | 46 Pd | 47 Ag | 48 Cd M | 49 In | 50 Sn | 51 Sb | 52 Te | 53 I M | 54 Xe |
| 55 Cs | 56 Ba | 57 La | 72 Hf | 73 Ta | 74 W | 75 Re | 76 Os | 77 Ir | 78 Pt | 79 Au | 80 Hg M | 81 Tl | 82 Pb M | 83 Bi | 84 Po | 85 At | 86 Rn |

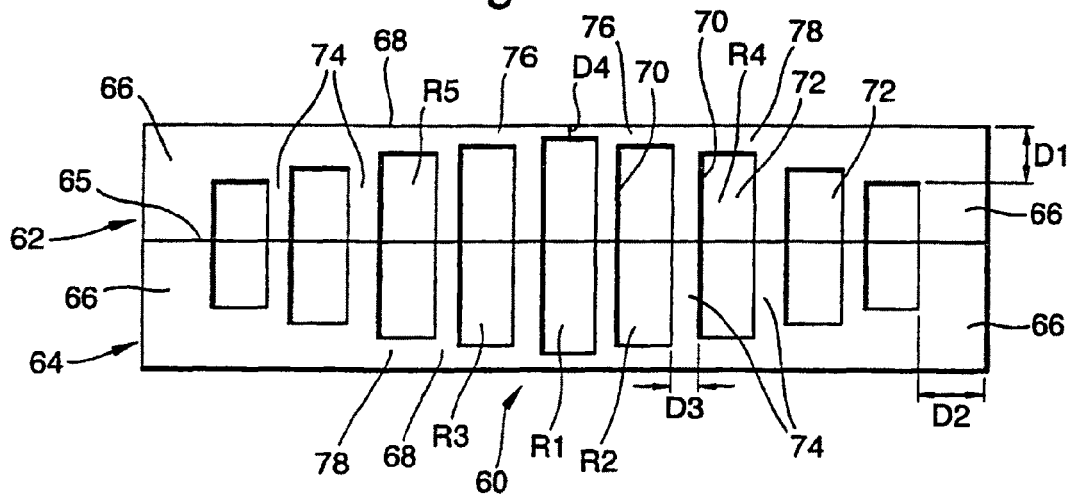
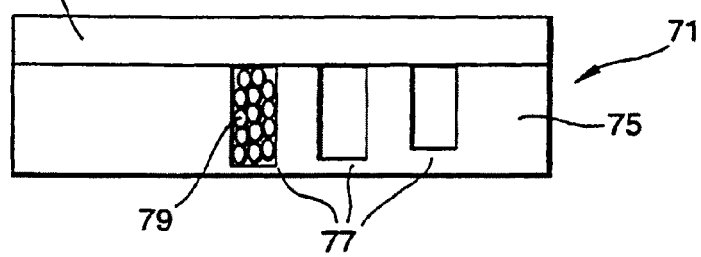
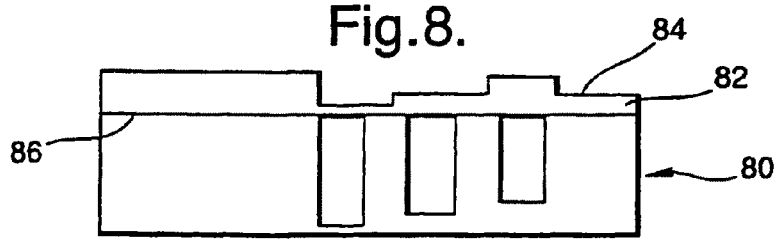
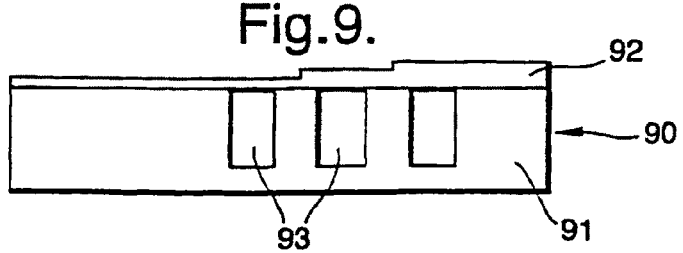

IMPLANTS FOR ADMINISTERING SUBSTANCES AND METHODS OF PRODUCING MESOPOROUS IMPLANTS

CROSS REFERENCE TO RELATED APPLICATION

This application is a continuation of application Ser. No. 09/647,599 filed Oct. 3, 2000 and now issued as U.S. Pat. No. 7,763,277, which in turn is a US national phase of PCT application Serial No. PCT/GB99/01185 filed Apr. 16, 1999 which in turn claims priority of GB Serial No. 9808052.6 filed Apr. 17, 1998, the entire content of which is hereby incorporated by reference in this application.

This invention relates to implants for administering substances. One embodiment of the invention is especially, but not exclusively, applicable to implants for administering micronutrient, or trace elements or minerals.

BACKGROUND OF THE INVENTION

Drugs are most often currently administered orally by the ingestion of tablets, capsules or aerosols, or via subcutaneous, intramuscular or intravenous injections or implants. Oral solid dosage forms account for 40-50% of the market, parenteral products—33% and the other more "novel" dosage forms (NDF's), only a few %. There is nonetheless enormous perceived potential for NDF's that can enhance a drug's therapeutic ratio and avoid patient non-compliance. Non-compliance remains a major issue despite 95% of patients being aware of its consequences. Common examples are incomplete courses of antibiotic therapy, using antidepressive drugs for too short a period, and forgetting to take contraceptive pills.

There are known implants that are implanted subcutaneously and which deliver a drug over a period of time in a controlled manner. These are typically based on polymer material systems. There are two basic types of implant for controlled drug delivery; "reservoir" and "monolithic" structures. "Reservoir" devices have layers which are corroded or absorbed by the body to release a depot of drug beneath these control layers. By having successive alternate control layers and drug layers the drug can be released over a period of time. "Monolithic" devices have the drug distributed throughout, so that release kinetics are controlled by slow corrosion and diffusion processes.

Problems include the so-called "burst effect" wherein an unwanted high fraction of the drug is released from the polymer capsule's internal surface quite soon upon in-vivo exposure. Another problem is the continuing need for high-purity, cost effective hosts that are capable of sustained drug delivery over months or years (for some applications).

Other known implants include inert ceramic implants which have the drug held in their pores, the drug having to leave the ceramic implant via a tortuous path of micropores, which delays its release and allows it to be controlled.

BRIEF SUMMARY OF THE INVENTION

This invention concerns slow-release tissue-compatible implants, particularly suited to delivering low payloads of a therapeutic substance to a specific site and/or over a long period of time ("long" may be months or years). Although delivered to the site of the implant the beneficial substance may be taken up by the body globally, and may have an effect at another site. In the past the major limiting factor for most drug delivery systems that use implanted materials (polymers or ceramics) has been the "payload" achievable. With the advent of new genetically engineered, more potent drugs (peptides, proteins, DNA fragments), miniaturised delivery systems are becoming more and more attractive, provided designs ensure patient safety. An example of such a safety issue for in-vivo administration would be the failure of an electronic "gate" linked to a large on-chip liquid reservoir. Such concerns can be addressed by the use of drug delivery arrays or drug incorporation within a resorbable host material.

The invention also concerns impregnation of porous semiconducting materials including porous silicon. It is advantageous to have implants comprising porous semiconducting materials that have been impregnated with one or more beneficial substances. It is also advantageous to have the concentration of such a substance or substances as high as possible and as deep as possible from the surface of the porous semiconducting material. A problem with prior art methods of impregnation, for example those disclosed in the paper entitled: "Impregnation of porous silicon" by R Herino (EMIS datareview on porous silicon (1997)) p66 or the paper entitled "Quenching of porous silicon photoluminescence by deposition of metal adsorbates" by D Andsager, J Hilliard, J M Hetrick, L H Abu Hassan, M Pilsch and M H Nayfeh, reported in J. Appl. Phys. (1993), 74, 4783, is that the depth of impregnation is very low, typically a few atomic percent at 300 nm or less.

BRIEF DESCRIPTION OF THE DRAWINGS

Embodiments of the invention will now be described by way of example only, with reference to the accompanying drawings, in which:

FIGS. 2A to 2D show scanning electronic micrographs at ×3000 magnification of a porous silicon implant explanted from a guinea pig at 0, 1, 4 and 12 weeks after implant respectively;

FIG. 5 shows a table of elements which may be administered using the present invention, those elements being indicated by the key as being essential trace elements, and/or having deficiency problems are those which are preferably incorporated in an implant;

FIG. 6 shows another embodiment of the invention in which there are a plurality of drug payloads provided on a resorbable tablet;

FIGS. 7 to 9 show alternative multi-drug tablet implants;

DETAILED DESCRIPTION OF THE INVENTION

Figure 1A:
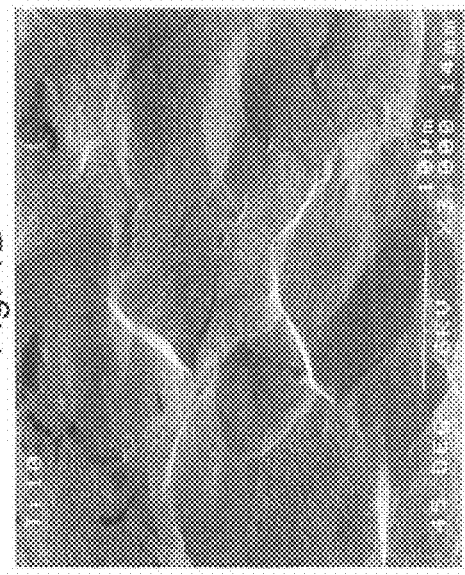
FIGS. 1A to 1D show scanning electronic micrographs at ×3000 magnification of a titanium implant explanted from a guinea pig at 0, 1, 4, and 12 weeks after implant, respectively.
Figure 1B:
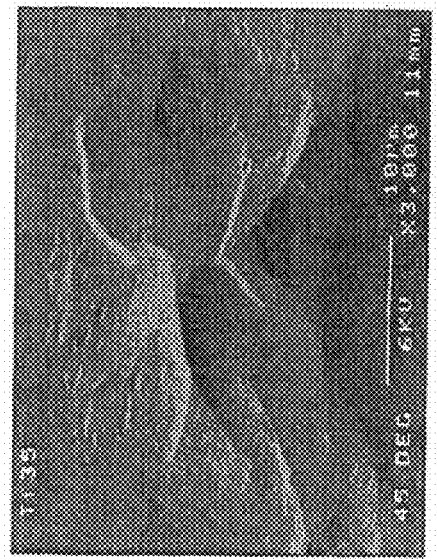
Figure 1C:
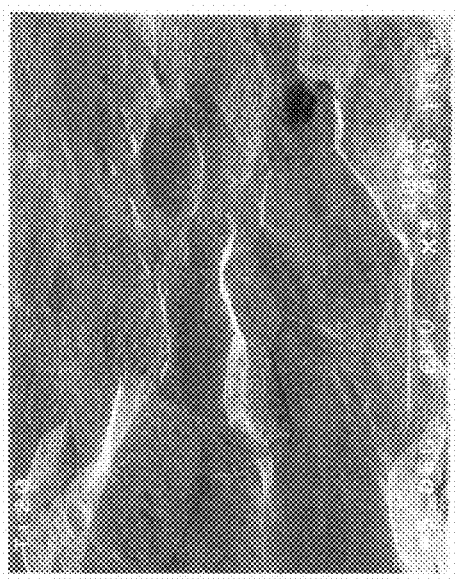
Figure 1D:
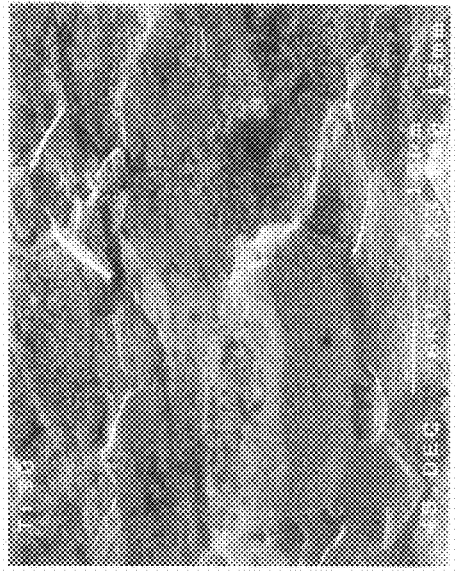
Figure 3B:
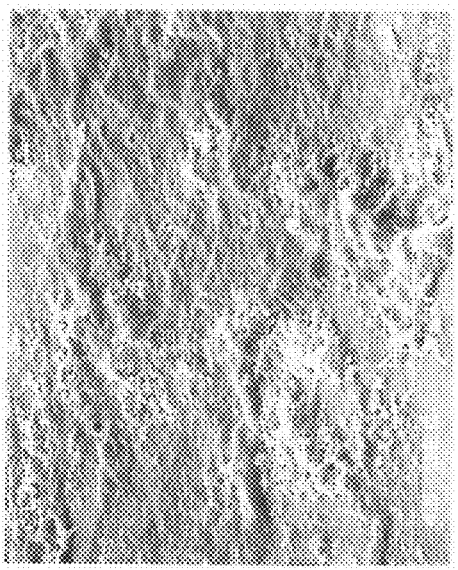
FIGS. 3A to 3D show scanning electron micrographs at ×3000 magnification of a porous silicon implant partially coated with hydroxyapatite (HA) and explanted from a guinea pig at 0, 1, 4, and 12 weeks after implant respectively.
Figure 3D:
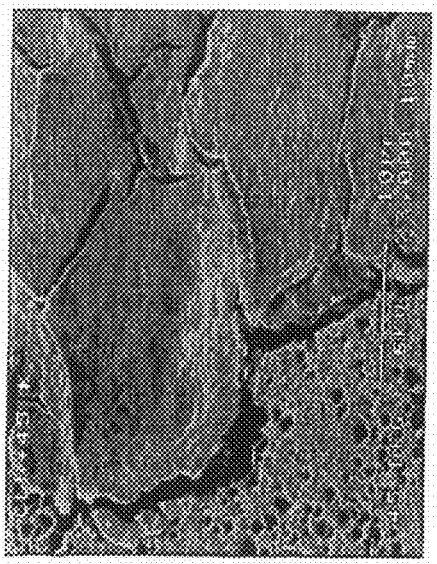
Figure 3A:
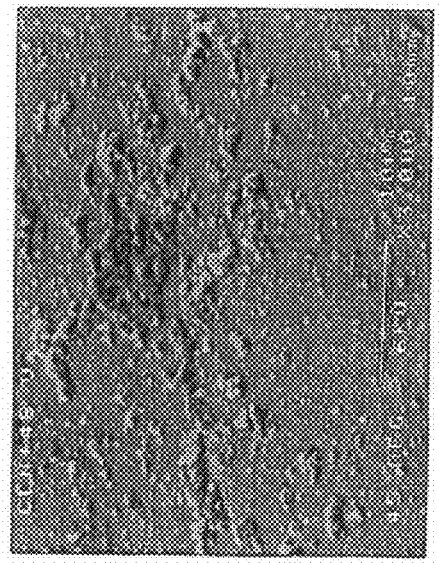
Figure 3C:
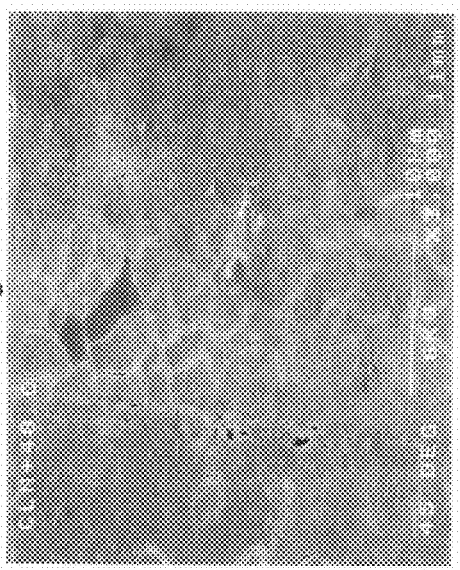

According to a first aspect the invention comprises a silicon implant provided with a substance to be administered to the implanted subject.

Preferably the implant comprises porous silicon. The porous silicon may have a porosity of at least 2%, 3%, 4%, 5%, 10%, 20%, 30%, 40%, 50%, 60%, 70%, 80%, or higher (the porosity is the fractional void content by volume). The porous silicon may have a porosity that is in a range between any two of the figures mentioned above. For example, the porous silicon may have a porosity between about 2% and 80%, or between about 4% and 50%, or about 30%.

The implant may have a coating, region, or layer of silicon, or it may be silicon substantially throughout its cross-section. The implant may have a layer of material over the silicon, for example a coating of hydroxyapatite. The over-layer of material may have a physiological effect upon implanting of the implant.

The silicon may be polycrystalline silicon.

Said substance may be distributed in the solid phase silicon material substantially uniformly. In the case of porous silicon said substance may be distributed in the pore network and/or in the silicon skeleton. It is envisaged that distributing the substance in the material of the skeleton may give greater control over the release rate of the substance since this will be related directly to the erosion rate of the silicon material. With a substance held in pores the release rate is also dependent upon how quickly the material can escape the pores (before the skeleton has eroded). This may or may not be desirable or acceptable. In the case of polycrystalline silicon the substance could be distributed in the grains and/or grain boundaries.

It has been appreciated that silicon, and in particular porous silicon, has very good properties which enable it to serve as a drug or micronutrient delivery vehicle. Experimental evidence in support of the suitability of porous silicon as a substance delivery vehicle in an implant has been obtained. Studies by the inventors have shown that porous silicon is "resorbable" or "bio-erodible", and is resorbed or eroded by the mammalian body at a slow enough rate to make long-term porous silicon implants a practical way to deliver drugs/substances.

Highly porous silicon has long been known to be unstable structurally and chemically, and researchers in the opto-electronics field have gone to great lengths to make it more stable for opto-electronic applications. It is ironic that the lack of stability/inert properties of porous silicon now, with hindsight, is a factor in the controlled delivery of substances by implants.

Tests show that high porosity (e.g. 80%) silicon is resorbed faster than medium porosity (e.g. 50%) silicon, which is in turn resorbed faster than bulk silicon (which shows little, if any, signs of being resorbed). Thus, by adjusting the pore size and total volume of pore to skeleton in porous silicon it is possible to tune the silicon material to be resorbed faster or slower.

Microporous silicon (pore size less than 2 nm), mesoporous silicon (pore size 2-50 nm) and macroporous silicon (pore size >50 nm) are all suitable carrier materials for erosion.

Silicon is cheap, and is available in very pure forms (e.g. the electronics industry already has a requirement for clean, pure, silicon wafers). Moreover, it is already known how to dope silicon crystals with a very wide range of elements, albeit in a different field and albeit at very low concentrations (lower concentrations than required for micronutrients).

It is envisaged that having a beneficial substance provided in porous silicon implant as a delivery mechanism will be especially appropriate for delivering substances which do not need to be delivered at high doses. It is envisaged that a porous silicon implant may be about 0.5×0.5×4 mm in size (or in the ranges >0 to 2 mm x>0 to 20 mm x>0 to 20 mm). Each implant may have a weight of less than a milligramme, or a few milligrammes, or a few tens or hundreds of milligrammes, and each tablet may conveniently be doped with a "dry payload" of tens to hundreds of microgrammes of substance, or even to a few milligrammes (or more if it is possible to carry it). This may be insufficient for delivery of macronutrients, or macro dose drugs, but it is sufficient to deliver substances which are needed in the micro to milligramme range.

One area where porous silicon is suitable as a carrier for a therapeutic or beneficial substance is in the provision of micronutrients or microminerals to subjects.

Some trace minerals needed by the body are present at extremely low concentration in the body (e.g. selenium, chromium, manganese and molybdenum). The recommended daily allowance (RDA) of microminerals can be <0.1 mg/day and yet deficiency effects are well documented (e.g. selenium iodine). This is often because only a small and highly variable fraction of orally-ingested microminerals are absorbed and hence become bio-available. Having these microminerals delivered by an implanted silicon tablet that is fully adsorbed is an attractive solution to deficiency problems. Moreover, by having the substances in an implant it is possible to deliver a substance to a specific site (e.g. iodine to or near the thyroid gland).

Silicon itself is an essential trace element, and a porous silicon implant could, of course, be used to deliver silicon in which case it may not carry any other beneficial substance.

The implant may have more than one beneficial substance. A multi-essential trace element implant having 2, 3, 4, 5 or more trace elements may be provided.

Other elements have widespread use clinically for therapeutic purposes, e.g. lithium for depression, gold and silver for antibacterial properties, and platinum for neoplastic diseases. These may be administered not so much to achieve a desirable "normal" mineral content in the physiology of a subject, but to increase levels of microminerals to therapeutic levels, possibly at a specific locality. The dose levels of such therapeutic elements in the blood stream are normally in the µg/l range, which is within the capabilities of porous silicon implants. The implant may comprise a porous silicon sample in which such an element (whether it be a trace element or an element in a beneficial substance or some other element of the periodic table) has been impregnated at a concentration between 1 and 90 atomic percent at a depth, from the surface of the sample, between 0.35 µm and 1000 µm. More preferably the element may be present at a concentration between 1 and 90 atomic percent at a depth, from the sample surface, between 1 µm and 1000 µm. Yet more preferably the element may be present at a concentration between 1 and 90 atomic percent at a depth, measured from the sample surface, between 10 µm and 1000 µm. Even more preferably the element may be present at a concentration between 30 µm and 1000 µm. It is often advantageous for such elements to be released into the body of the mammal at a slow rate. To facilitate this slow release it is advantageous to provide high concentrations of such elements at relatively large depths from the surface of the porous silicon.

A therapeutic or essential trace element (or other element) may be delivered in non-elemental form. For example, a salt of a metal may be the beneficial substance, metal ions being available to the body of the patient. So long as the substance is delivered in a physiologically usable form, how it is carried in the erodable material (compounded or elemental) may not matter.

It will be appreciated that implanting an implant which can deliver a controlled amount of a drug/micronutrient/micromineral for a month, or even two or three months, or a year, or possibly even years, has great advantages over relying on a patient to eat correctly or take oral tablets correctly, especially when the disorder being treated exacerbates any difficulties in the patient having a discipline to take the remedy. The fact that a silicon implant can be made to break down slowly makes it possible to leave an implant alone for a long time. When a sustained level of drug dose delivery is required a silicon implant can be engineered to deliver a prolonged sustained substantially constant (or constant enough for the intended purpose) level of drug or mineral. Using implants to deliver trace elements is attractive for those people who have gastrointestinal tract disorders and who cannot absorb some elements orally. Even if a patient were to be treatable orally there can be a great variation in the level of absorption achieved in people's guts and the same level of oral dietary supplement may result in different levels of absorbed mineral. Subcutaneous absorption has significantly less variation between people and is therefore more easily controlled.

A feature of virtually all drugs, especially large organic molecules, however is that they cannot survive high temperatures. If a silicon implant is made using high temperature doping techniques it may not be possible to get the structural silicon material of the implant to take up some molecules in a functional state. However, this is not a problem for therapeutic elements (e.g. Li, Se, etc.).

Of course, it is possible to use techniques other than thermal drive in to get drugs into the depths of an implant and/or into the solid phase of the porous skeleton. We could use vacuum evaporation, or build the implant up in layers, with the substance adhering predominantly to the surface of each layer, or indeed any suitable technique for distributing the substance throughout the body of the erodable implant.

The geometric design of known monolithic drug release implants can be used to control the drug release rate, and similar techniques of geometric design can be used to control substance release from silicon implants. This may be in addition to controlling the porosity, and pore size of porous silicon to control the rate of dissolution of the implant. The implant may have different porosity at different depths.

Of course, the silicon implant need not necessarily have its erodable carrier material of pure silicon, or substantially pure silicon. Now that it has been established that silicon works it is predictable that silicon carbide and silicon nitride may also have similar properties. Indeed, as a generalisation, a silicon-based compound which has the corrosion properties desired (corroding at a generally constant rate over months or years) and which is non-toxic at the levels released, and which otherwise has no unacceptable harmful effects, would be suitable in place of pure (or substantially pure) silicon as the carrier material, but silicon is still currently preferred.

According to a second aspect the invention comprises a porous or polycrystalline implant provided with a substance to be administered to the implanted subject, the implant being made substantially of an element.

Preferably the implant is made of porous or polycrystalline semiconductor.

Although tests by the inventors in vivo show that porous silicon is corroded if subcutaneously implanted, the inventors also have in vitro tests using simulated body fluid (SBF) which shows that porous and polycrystalline silicon behave in a similar way in SBF.

The realisation that silicon, and especially porous silicon and/or polycrystalline silicon, are suitable materials to be bio-eroded by the body in a controlled manner, and the realisation that this can be used to release drugs/substances into the body (or to a localised area), can be further expanded. The implant may have a plurality of drug payload areas defined in a body of silicon, the body of silicon having a plurality of barrier regions, or doors, adapted to be resorbed in use by the body, the geometry and size of the barrier regions being such that in use at least a first barrier region is eroded or resorbed such that the drug payload in the drug payload area adjacent said first barrier region is released to the body before a second barrier region, adjacent a second drug payload area, is resorbed sufficiently to enable the second drug payload to be released, thereby providing a time-differential breakdown of at least the first and second barrier areas and hence a sequential release of said first and second drug payloads.

The first and second drug payloads may comprise the same drug, or different drugs.

There may be three or more barrier regions each adapted to be corroded at different times, and adapted to release drug payloads from respective drug payload areas at different times.

The barrier regions may comprise porous silicon, such as mesoporous silicon or microporous silicon. The barrier regions may comprise polycrystalline silicon. The rate of erosion of the silicon can be controlled by controlling the porosity (higher porosity materials are corroded faster) and the pore size (smaller pores for same porosity are corroded faster), and the barrier thickness.

Instead of having one implant with a plurality of drug payloads it may be desirable to provide a plurality of separate implants with drug payloads and barrier regions adapted to release the drug payloads at different times.

The implant may comprise a tablet. The tablet may comprise an array of drug payload reservoirs each containing a respective drug payload. The tablet may have a longitudinal direction and the respective barrier regions associated with respective drug payloads may be spaced apart in the longitudinal direction. The implant may be adapted to be corroded in a direction transverse to the longitudinal direction, and preferably at right angles to it, in order to release the respective drug payloads. The implant may have a longitudinally extending surface portion and the drug payload areas may be separated from the surface portion by barrier regions requiring different times of attack by body fluids to be corroded. The different corrosion times of the different barrier regions could be afforded by different thicknesses of barrier region. Alternatively, or additionally, the silicon material of the implant may have different corrosion properties at different barrier regions (e.g. they could be made of porous silicon of different porosity).

According to a third aspect of the invention a method of impregnating a porous semiconducting material with a impregnate substance is provided, the method comprising the step of bringing the impregnate substance into contact with the porous semiconducting material; characterised in that the method further comprises the steps:
  (a) causing the impregnate substance to be in a molten phase; and
  (b) allowing the molten impregnate substance to pass into the porous semiconducting material.

It is advantageous for some applications, for example medical applications, to have a method of impregnating substances at a depth of at least several hundred nanometers below the surface of a porous semiconducting sample. It has been found that high depths of impregnation can be achieved by ensuring that the substance to be impregnated is in a molten phase.

Preferably the method of impregnating a porous semiconducting material further comprises the step of thermally decomposing the impregnate substance that has passed into the porous semiconducting material.

Advantageously the method of impregnating a porous semiconducting material comprises the step of reacting the impregnate substance that has passed into the semiconductor material with an oxidant, such as oxygen.

The impregnate substance may be fixed to the porous semiconductor by thermally decomposing it once the substance has entered the interior of the semiconductor. Alternatively the impregnate substance can be fixed to the porous semiconductor by reacting with an oxidant such as oxygen.

Throughout the specification the term "sample surface" is to be taken to mean the surface that separates the sample of porous semiconductor (including porous silicon) from its surroundings. The term does not mean the surfaces that define the pores, unless such surfaces form part of the surface that separates the porous semiconductor from its surroundings.

According to a fourth aspect the invention provides a sample of porous silicon that has been impregnated with an impregnate substance, the sample having a sample surface and the impregnate substance comprising an impregnate element, characterised in that the impregnate element is present at a concentration between 1 and 90 atomic percent at a depth, from the sample surface, between 0.35 µm and 1000 µm.

With reference to the drawings, FIGS. 1A to 1D show that over a 12-week period of tests a titanium implant subcutaneously implanted in a guinea pig exhibits little change to its surface—it is bioinert.

FIGS. 2A to 2D show that when a porous silicon subcutaneous implant (30% porosity) is examined at 0, 1, 4 and 12 weeks there are substantial changes to the porous surface of the implant. There is considerable corrosion of the porous silicon, even to the extent that the layer of porous silicon above the bulk silicon body (upon which the porous silicon is formed) was totally eroded at places.

The discs used in the in-vivo trials were made as follows:
(a) Titanium Discs

Titanium foil of 99.6+% purity was purchased from Goodfellow Metals Limited in the form of punched-out discs of 0.5 mm thickness and diameter 11.5 mm. These were subsequently abraded (on both faces) with 12 µm diamond powder to remove any burrs introduced by the punch-out process and to develop equal degrees of surface roughness on both faces. Batches of 10 discs were then chemically etched at a time after cleaning in an ultrasonically agitated acetone bath for 20 minutes. The discs were isotropically etched (to remove surface damage) for 2 minutes in a stirred solution of 35 ml $H_2O$, 10 ml $HNO_3$ and 5 ml 40% HF. The etch process was quenched with DI water and discs were thoroughly rinsed in DI water prior to drying on filter paper.
(b) Bulk Silicon Discs Batches of 12 mm wide discs were sawn out of ~5" (100 mm) diameter CZ wafers ($N^+$, phosphorous-doped 0.0104.0.0156 Ωcm resistivity, 0.5 mm thick, (100) orientation) using a custom-built drill bit. Discs were cleaned in "meths", then ethyl acetate and then in an ultrasonically agitated acetone bath. Smoothing of the disc edges, removal of saw damage and equality of surface roughness on both faces was achieved using a "polish etch": 25 ml $HNO_3$+5 ml HF (40%)+5 ml acetic acid. Batches of 10 discs at a time were given a 5-minute etch with continuous stirring followed by a DI $H_2O$ quench and rinse with drying on filter paper.
(c) Porous Silicon Discs The chemically polished bulk Si discs were anodised sequentially, one at a time, in a custom-built electrolytic cell that enabled both faces and edges to be porosified. Discs were held at one edge by a platinum "croc-clip" and lowered and raised in a controlled manner by a stepping motor into electrolyte in a cylindrical Pt crucible that formed the cathode. Each disc was anodised potentiostatically (i.e. at a constant voltage of 1.0 V) in 40% aqueous HF for a period of 10 minutes. With this type of arrangement most current flow occurs via the meniscus, so the procedure adopted was to slowly raise the meniscus up to the centre of the disc, remove the half-anodised disc, dry it and then invert it, to anodise its other half in the same manner. Fully anodised discs were by this process completely covered in an ~30 µm thick coating of porous silicon. They were rinsed in DI $H_2O$ and dried on filter paper.
(d) Sterilisation All discs were stored in air prior to sterilisation by "autoclaving" at 134° C. for 10 minutes in pressurised steam.

FIGS. 3A to 3D show similar corrosion/resorbtion of coated porous silicon, 30% porosity, (coated with hydyroxapatite). The rate of corrosion appears to be slower for the coated porous silicon. Coating the silicon with other materials may delay, or speed up corrosion at early stages, depending upon the coating material used. This can be used to give a high initial dose of substance and then a lower dose (possibly for a prolonged time), or a low initial dose (or no dose) initially, followed by a higher dose later.

FIGS. 2 and 3 show that the corrosion of porous silicon in mammals does take place, and in a progressive manner.

Tests were also done to ensure that the silicon implants did not cause any serious problems to the guinea pigs, and again these tests show that using silicon, and especially porous silicon, as a biologically acceptable material is viable in a subcutaneous site. The pathological test results are given in the sections, presented below, entitled "Inivo trial of Porous Silicon Implant" and "Score grades" which forms part of this patent application.

The 12-week tests described above have been followed by a 26-week study which has shown entirely consistent results: there is a steady corrosion of porous silicon, and the corrosion of the implants did not cause any significant harmful effects on the test subjects. There was no gross inflammatory response, no significant fibrotic scarring, and excreting the corroded silicon was not a problem.

Since the corrosion of polymer is known and tested as a delivery mechanism for drugs, the present invention is, with the support of the tests discussed, fully realisable. Nevertheless the concept of using semiconductor tablets for prolonged in-vivo drug delivery is completely novel.

Figure 4A:
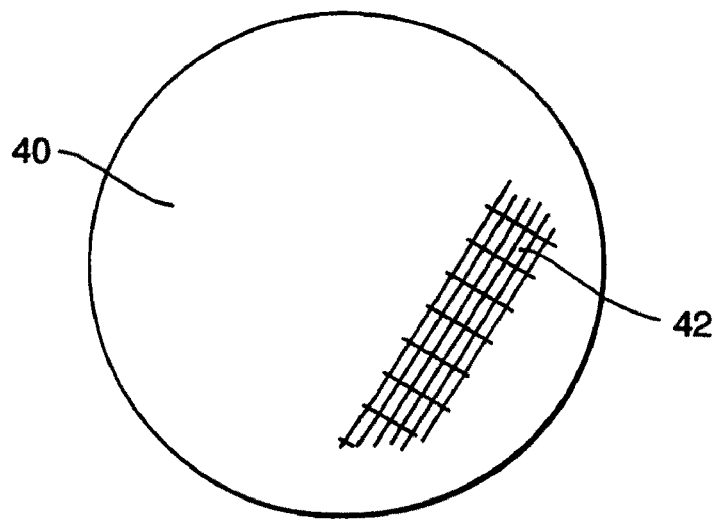
FIG. 4A shows schematically a silicon wafer micromachined to form thousands of implants.

FIG. 4 shows a silicon disc 40 machined to produce many thousands of implant tablets 42. It is envisaged that hundreds or thousands of tablets could be made from an 8 inch (200 mm) diameter wafer.

The wafer is treated so as to cause it to become porous throughout its depth, and then broken into discrete tablets. The tablets are then smoothed to facilitate subcutaneous insertion and acceptability. An elongate tablet, such as that shown, may be suitable for injection through a needle. The rounded ends 44 of the elongate tablet may help this. The tablets may take the form of that shown in FIG. 4B.

Figure 4B:
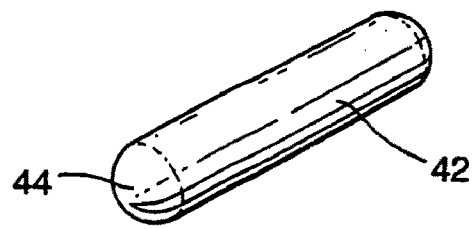
FIGS. 4B and 4C show two implant structures.
Figure 4C:
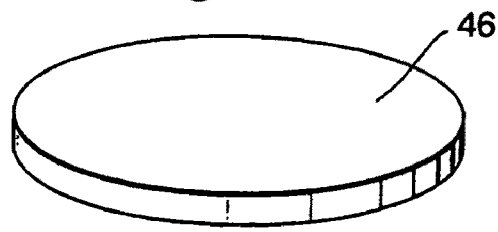

In an alternative arrangement shown in FIG. 4C a disc 46 of about 20-25 mm diameter is shown. This is surgically subcutaneously implanted.

It will be appreciated that the implants 42 and 46 are completely eroded in the body and do not need surgically removing.

FIG. 5 shows elements considered suitable for incorporation into silicon implants which rely upon the corrosion/resorbtion of the silicon material to deliver an active substance (the element). It is envisaged that implants will be provided having one or more of the elements indicated as being essential trace elements, and most preferably those indicated as being essential trace elements with deficiency problems.

It is also, of course, envisaged to administer therapeutic elements or substances for particular disorders.

Furthermore, in the case of a problem associated with an excess of an element, or excess of a substance, the implant could be used to administer a blocker to prevent the excess substance operating properly, or something to bind to or react with the excess substance, reducing the effective excess. For example, it has been proposed that silicon in the form of silicic acid can beneficially assist in aluminium excretion.

There is no theoretical reason why an element such as iron cannot be administered using the present invention, but it may as a practical matter be difficult to get a sufficiently high dose of Fe into a silicon tablet to make it sensible to implant an implant.

Elements which are preferred for incorporation into a silicon micromineral tablet include: Vn, Cr, Mn, Se, Mo (dietary requirements), Li, Ag, Au, Pt (therapeutic effect).

As well as silicon other suitable biocorrodable semiconductors to use as carriers for beneficial substances include germanium, silicon carbide and silicon nitride. The semiconductor material could be doped or undoped. Silicon carbide may have anti-thrombogeric properties, and silicon nitride may have orthopaedic applications.

There is no reason why molecules, as well as elements, cannot be delivered, so long as the technique for getting the drug/desirable substance into the implant does not destroy the efficiency of the substance, and so long as they are released in a form which is active when the silicon is broken down.

In the case of minerals/trace elements one way of producing micromineral tablets is:

(1). create porous silicon: for example by anodising a whole silicon wafer to introduce a low concentration of mesopores (e.g. 30% porosity)—this is done using HF acid and an electric potential in a known manner (see for example U.S. Pat. No. 5,348,618 which discusses creating porous silicon using HF acid to achieve partial electrochemical dissolution—the contents of U.S. Pat. No. 5,348,618 are hereby incorporated by reference);

(2). use wafer dicing and wet-etching techniques that are standard in the silicon semiconductor industry (or any other techniques) to define smooth tablets (sharp edges are undesirable);

The order of (1) and (2) may be reversed.

(3). impregnate the tablets: for example by immersing them in an aqueous solution of the mineral, or minerals, to be impregnated (the tablets could contain more than one mineral) and then driving in the minerals using a thermal drive-in technique, for example put the saturated tablets in an oven at 800° C. for thirty minutes;

(4). clean the tablets (if necessary).

Another way of getting a substance into the implant is to put a salt of a mineral on the surface, heat in an inert atmosphere (e.g. argon) until the material melts and wets the porous structure. The insert/wafer can then be cooled down, and any excess substance washed off in water. A thermal drive in operation can then be performed.

It is preferred to drive the mineral into the solid phase of the porous structure, rather than leave it solely in the pores. This gives greater control of the dissolution rate of the mineral and eliminates the "burst-effect" problem common with polymer-based systems.

A combination of a knowledge of the dissolution rate of the tablets, and how that behaves with time, and the doping level of the tablets, and how uniform that it, gives the ability to control the dosage of substance administered over time.

FIG. 6 shows a schematic cross-section of a multi-reservoir silicon tablet 60 (not to scale). The tablet 60 comprises a first portion 62 joined, for example by medical adhesive (or by wafer bonding), to a second portion 64 at interface 65. In this example, the first and second portions are mirror images of each other, and are identical (they are symmetric). Each half 62 or 64 of the tablet has side peripheral, or rim, portions 66 and a top (or bottom) wall portion 68. Each half of the tablet has micromachined in it a large number of reservoirs 70 which, in the assembled finished tablet, contain drug material 72. The reservoirs are separated by island walls 74 of silicon. The tablet 60 (including the rim portions 66, top/bottom portion 68, and island walls 74) is made of resorbable porous silicon which is corroded and absorbed by the body when implanted. The fact that the two portions 62 and 64 are substantially identical makes it cheaper to manufacture them since there is only one shape to machine.

In the example shown in FIG. 6, distance D4 is shortest and the wall thickness in the region D4 is breached first by corrosion of the porous silicon, releasing the contents of reservoir R1 first. Next reservoirs R2 and R3 are released as the next thinnest wall portions 76 in those regions corrodes away and is breached. Then wall portions 78 corrode releasing the contents of reservoirs R4 and R5, and so on.

By having barrier walls of different thicknesses it is possible to achieve controlled—and sustained—drug release as reservoirs are sequentially opened.

The distances D1, D2 and D3 are such that the "lid" thickness D4 is significantly thinner than the rim thickness D2. Thus, the micromachining of the depths of the reservoirs controls the release time of the outer reservoir, rather than its proximity to the peripheral edge of the silicon wafer. Similarly, D3 is large enough between adjacent reservoirs that it is the "lid" thickness that is corroded first, and not the island walls 74 between adjacent reservoirs (after one reservoir has already been opened to body fluids corrosion of the island walls occurs).

Of course, we may prefer to have the progressive opening of reservoirs achieved by corrosion of the dividing walls between adjacent reservoirs, instead of or in addition to the corrosion of peripheral surfaces of the tablet.

It will be appreciated that the reservoirs of drug material could hold beneficial substance in any form, for example liquid drug, or powder drug, or solid drug. The drug could be a complex organic molecule, or it could be a micronutrient or micromineral as previously discussed.

The reservoirs of drugs could contain a micromineral tablet, or other tablet/implant. A reservoir hole may contain a plurality of erodable drug/element delivery tablets/implants, which may contain the same or different beneficial substances, and/or may be corroded at different/the same rates. Thus, the doors to reservoirs may be separately eroded to allow physiological access to tablets which in turn release a beneficial substance in a controlled manner over days, weeks or months. There may be several tablets in a reservoir, or tens of tablets, or hundreds of tablets.

The "reservoirs" need not necessarily be machined holes in a body of resorbable porous silicon material, they could be regions which have been differentially impregnated with a beneficial substance in comparison with the "walls" (or they could be regions which otherwise have a differential level of beneficial material in comparison with the "wall" regions). Thus, the implant may be a solid body (possibly made from discrete sections, but with no actual holes). However, at present, it is envisaged that micromachining an array of holes will probably be best.

The wall regions can be considered to be time delay means adapted to delay the timing of release of the contents of the reservoirs.

It will be appreciated that silicon technology is indeed ideally suited to compartmentalising drug payloads—an attribute that is exploited in this invention. The basic idea is to micromachine an enormous number (e.g. $10^2$-$10^4$) of independent reservoirs into resorbable blocks of Si, thereby generating a new way of controlling kinetics of drug release. The time of release from each reservoir is predetermined by the overlying thickness of a microporous "lid" that is gradually eroded in-vivo.

The example of FIG. 6 may be created by anodising right through two Si wafers, then deep dry etching an array of photolithographically defined cavities in both, and finally bonding them together after reservoir filling. The kinetics of release are determined by the volume distribution and lid thickness distribution within the array. For this to be the case the diffusion time of a high molecular weight drug (which may be a typical drug) through the "lid" is made infinitely long compared with its erosion rate. This is achieved via lid topography (use of micropores <2 nm width) or pore surface chemistry (e.g. hydrophobicity with hydrophilic drugs). Alternatively the drug deposit is itself in solid form until the physiological fluids break through into the reservoir.

The arrangement of FIG. 6 is one way of providing a multi-reservoir, time-differential release implant. Similar effects can be achieved by the implant 71 of FIG. 7 which shows a lid 73 made of very slowly corroded material and a base 75 made of faster corroding material. A flat interface between the lid 71 and the base 73 may make it easier to assemble the implant. The depths referenced 77 control the release time of the reservoirs.

One of the reservoirs in FIG. 7 is shown containing a number of micromineral porous silicon tablets 79. The lid 73 could, of course, be made of a material that corrodes at the same rate as the base (e.g. of the same material).

FIG. 8 shows an arrangement and a flat lower surface 86. The profile of the lid matches the "doors" of the base so as to achieve breakthrough of the lid and base at regions adjacent any particular reservoir generally at the same time.

FIG. 9 shows an implant 90 having a base and a lid 92. The base 91 has reservoirs 93 of generally the same depth, and barrier regions 94 of generally the same depth. The lid 92 has a stepped/profiled upper surface topography arranged to ensure sequential, time-differentiated, breakthrough into the reservoirs (the lid is corroded through first, not the base).

The multi-reservoir implanted discussed are all fully resorbable, and do not require surgical removal, but the invention is also applicable to non-corrodable implants having corrodable doors. The non-corrodable part of the implant may be bulk silicon.

The above types of delivery system offer much better control and predictability of delivery rates than conventional "monolithic" polymer systems. In the latter case drug release rates are often determined by diffusion through a tortuous pore network, at least for sustained release.

It will also be appreciated that the technical effect achieved by the embodiment of FIGS. 6 to 9 can be achieved using other corrodable materials beyond silicon. Indeed, in one aspect the invention is not restricted to silicon material for the construction of a multi-reservoir progressive drug release implant. Any suitable material may be used.

According to another aspect the invention comprises an implant having a plurality of reservoirs, a plurality of beneficial substance charges provided on said reservoirs, and a plurality of barrier regions, or doors, provided adjacent said reservoirs, the doors having a plurality of different erosion times when implanted, the arrangement being such that in use the doors are broken down sequentially in order to stagger the release of the contents of the reservoirs.

There may be up to ten reservoirs, of the order of tens of reservoirs, or even of the order of hundreds of reservoirs, or more.

The invention also comprises a method of timing the release of beneficial substances in an implant.

The fact that silicon does not resorb too quickly is beneficial. It is preferred to have an implant that will not need replacing for at least one month, and most preferably for at least two months, three months, four months, six months, nine months, or a year or more.

A problem with using the erosion of an implant to deliver drug embedded in the material of the implant is that the surface area of the implant changes with time (or can change with time) and hence the drug delivery changes with time. For example, a sphere gets smaller. This can in part be countered by the geometric design of the implant to allow the creation of an expanding internal surface to compensate for a contracting external surface.

An alternative, or complementary, approach that is now realisable with porous silicon, and with polycrystalline silicon, is to ensure that the drug/beneficial substance is present at different concentrations at different regions of an implant. This can be achieved by controlling the pore size through the depth of a body of porous silicon, or by controlling the grain size/number of grain boundaries. The number and/or size of grain boundaries may be controlled throughout the depth of a body of polycrystalline silicon. Thus, it is possible to have a porous silicon tablet which has a substantially uniform dose delivery rate with time as it is resorbed due to the concentration of drug/micromineral in it increasing towards its centre so as to balance the decrease in exposed surface area.

It will be noted that substantially 2-dimensional shapes, such as a disc, do not suffer so much from changes in surface area, and neither do the elongate "line" shapes (as shown in FIGS. 4B and 4C).

In addition to the porosity affecting the amount of substance that can be held in microporous silicon (greater porosity, greater substance-containing capability), the pore size can affect the rate of dissolution of the implant. Thus, the inner regions of a porous silicon implant can be arranged to corrode faster than the outer regions, again having a compensating effect for the loss of exposed surface area.

Whilst many countries do not, yet, permit the patenting of methods of treatment of the human or animal body by surgery or therapy, there are some (e.g. USA) who do. In order for there to be no doubt about the Paris Convention priority entitlement to such an invention in those countries that do permit it, the invention also comprises the treatment, therapeutic or prophylactic, of a disorder of the human or animal body by implanting a silicon implant and allowing the implant to corrode or be resorbed so as to realise a beneficial substance which helps to alleviate or ameliorate the disorder, or to prevent the disorder from occurring. The implant will typically be implanted subcutaneously.

Furthermore, the technique could be used to release diagnostic substances, possibly in a localised region of the body. Diagnostic substances are "beneficial substances".

It will be appreciated that the realisation that silicon structures, especially porous silicon and polycrystalline silicon structures are able to be broken down by the body over a long (months) period of time without evidence of significant harmful effects has led to the ability to create beneficial substance (e.g. micronutrients and drug) delivery implants which take advantage of this. The evidence showing no detrimental effects of implantation enables us to have a reasonable and predictable expectation of success—it is more than speculation.

At present, it is perceived that restrictions on the physical size of the drug payload for implants will restrict their practical use to delivering microminerals, or other substances, which are not required at high levels (e.g. genetically engineered proteins, peptides, and gene fragments, and other DNA material). However, the invention is not necessarily to be restricted to those areas if a practical macro-drug delivery implant is created.

A "beneficial substance" is something beneficial overall: it could be a toxin toxic to undesirable cells/to interfere with an undesirable physiological process. For example, anti-cancer substances would be considered "beneficial", even though their aim is to kill cancer cells.

It will be noted that the terms "eroded", "corroded", "resorbed" are all used herein. The mechanism of corrosion is not fully known, but that erosion, corrosion takes place is proved. Bioerosion, bioresorption, biodegradation are other possible terms: at present whether the silicon/carrier material is taken up into cells or stays extracellular is not considered important. It is not intended, necessarily, for the invention to be restricted to any precise biological distinction between the "corrosion" terms used.

Impregnation of Porous Semiconducting Materials

Experiments were carried out to demonstrate the impregnation, according to one aspect of the invention, of porous silicon samples with a number of metals (manganese, silver, and chromium) or compounds (for example oxides) of these metals. A salt of the metal was placed on the surface of a sample of porous silicon. The temperature of the salt was raised until the salt melted. The molten salt then passed into the bulk of the porous silicon. The application of heat resulted in decomposition of the salt to yield the metal or the metal oxide.

The starting material was 3-5 ohm cm n-type (100) silicon. This was anodised in a 50/50 mixture by volume of ethanol and 40 wt % hydrofluoric acid. The anodisation current was 100 mAcm$^{-2}$ and the anodisation time was 5 minutes. This gave a porous silicon film of thickness 30 microns and gravimetrically determined porosity of 38%. Samples of the porous silicon (supported on the un-anodised bulk silicon) prepared by this method, were cleaved to make pieces approximately 2 cm by 2 cm in dimension.

The metal salts chosen were the manganese (II) nitrate, chromium (III) nitrate, and silver (I) nitrate. A general procedure, according to one aspect of the invention, was adopted. The nitrate was placed on the surface of the porous silicon sample. The sample of porous silicon was placed on a graphite block with the porous face upwards. On to the surface was placed an amount of the metal nitrate powder. The graphite block, with the porous silicon wafer on it, was loaded into a CVD reactor. The reactor was assembled and closed to the atmosphere. The CVD reactor was flushed with argon (to create an inert atmosphere) or hydrogen (to create a reducing atmosphere).

The sample temperature was then raised until the metal nitrate was observed to melt.

For some samples, following a period at this initial temperature, the temperature was raised further and the salt observed to decompose by the evolution of bubbles. After some time at elevated temperature the sample was cooled to room temperature and removed from the CVD reactor. A number of the samples produced by this method were then washed in deionised water and dried. After washing, analysis of the metal content was performed by EDX on cleaved edges.

For each impregnation procedure, the sample of porous silicon was weighed prior to impregnation. After impregnation the samples were washed in deionised water and re-weighed. For each of the three nitrate salts tested, an increase in weight was observed. Since the three nitrate salts are all highly soluble in water, the increase in weight suggests that the nitrate salts were decomposed, presumably to either the metal or an oxide of the metal, by the heat applied to the porous silicon sample.

The procedure for managanese (II) nitrate, which is consistent with the above mentioned general procedure, will now be described. Manganese nitrate powder, sufficient to give approximately 0.5 gram of powder per 1 cm$^2$ of porous silicon surface, is placed on the surface of the porous silicon sample. Inert gas (argon) at a rate of 700 cm$^3$/min was allowed to flow through the CVD reactor for ten minutes. At this point the temperature of the graphite block with the wafer upon it was raised to 50° C. The manganese nitrate was observed to melt and the temperature was maintained at this value (50 C) for one hour. The temperature was then raised to 150° C. and maintained at this value for a further hour. At this stage gas evolution from the molten salt was observed. The temperature was then allowed to cool to room temperature and the sample removed. The sample was then washed by immersion in deionised water for about 5 minutes. This was observed to remove most of the salt remaining on the surface of the porous silicon. Samples for elemental analysis were then cleaved from the sample.

The porous silicon sample, which had been treated with manganese nitrate, was washed in water to remove any excess of the unreacted salt on the surface although a clearly marked area was left which indicated where the salt had melted on to the porous silicon substrate. Elemental analysis on a cleaved section (the cleaving occurring at or close to the boundary between the porous and bulk silicon) through the sample was then used to reveal the extent of the manganese impregnation. In all cases, for the manganese, the metal or more probably the metal oxide had reached the bottom of the porous layer, a distance of 30 μm with the substrates used in these experiments. Manganese was observed only under the area where the molten salt had been. The composition even at the bottom of the pores was sufficient for it to be easily detected by EDX suggesting that it was in excess of one atomic percent. It should be noted that the technique of EDX only allows concentrations of metal in excess of one atomic percent to be detected. For treatment with manganese nitrate, the above procedure was carried out in both a hydrogen atmosphere and in an argon atmosphere. In both types of atmosphere similar concentrations of manganese atoms were observed at similar depths.

The procedure for chromium (II) nitrate, which is consistent with the above mentioned general procedure, was identical to that described for manganese (II) nitrate given above except that the graphite block was heated to 90 C to cause melting and after one hour this temperature was raised to 150 C and maintained at this value for a further hour. The procedure for silver (I) nitrate, which is consistent with the above mentioned general procedure, was identical to that described for manganese (II) nitrate given above except that the graphite block was heated to 250 C to cause melting and after one hour this temperature was raised to 450 C and maintained at this value for a further hour.

EDX analysis for samples of the chromium and silver nitrate treated samples was carried out in a similar way. The treated porous silicon sample was washed in water to remove any excess of the unreacted salt on the surface. Elemental analysis on a cleaved section (the cleaving occurring at or close to the boundary between the porous and bulk silicon) through the sample was then used to reveal the extent of the impregnation of the salt. Chromium oxide (for the chromium nitrate treated sample) had reached the bottom of the porous layer, a distance of 30 µm with the substrates used in these experiments. Silver (for the silver nitrate treated sample) had reached the bottom of the porous layer, a distance of 30 µm with the substrates used in these experiments. Unlike the cases of the manganese and chromium treated samples, silver was distributed throughout the pore structure and not just in the area under the melt. The composition even at the bottom of the pores was sufficient for it to be easily detected by EDX suggesting that it was in excess of one atomic percent.

The impregnation procedure for manganese was also carried out in ambient air. Manganese nitrate was placed on the surface of a porous silicon film; the film being placed on a standard laboratory hotplate. The sample was heated on a hotplate to 56 C for 70 minutes and 150 C for 70 minutes. This gave a black film on the surface of the porous silicon layer. EDX analysis of this film revealed manganese at greater than 1% throughout the layer. There was also a band of higher concentration (a few atomic percent) at a depth of a few microns.

Similar methods to that described here could be used to pass impregnate substances other than metal salts into any porous semiconductor (porous silicon materials being a subset of porous semiconductors). The impregnate substance could be a metal salt (including the metal nitrates described here) and/or a beneficial substance. The impregnate substance could be an element of the periodic table. Samples of porous silicon, having a sample surface and impregnated by identical or similar methods to those described here, could be used as a component in implants described at other parts of this application.

Invivo Trial of Porous Silicon Implant

The purpose of the trial was to evaluate the biocompatibility of porous silicon when implanted at subcutaneous sites in guinea pigs in order to investigate the materials' suitability for use in implantable devices. The trials were carried out over 1, 4, 12, and 26 weeks.

Experiments were conducted in accordance with the methods specified in the International Standard for biological evaluation of medical devices part 6 (ISO 10993-6).

The test specimens were in the form of discs (10 mm in diameter, 0.3 mm in thickness). Manipulation of their surface characteristics aimed to make 1 specimen type bioactive (ie encourage tissue attachment; hereafter termed porous silicon), 1 specimine type bioinert (ie produce no interaction with living tissues; hereafter termed bulk silicon) and 1 specimen type bioactive pre-coated with hydroxyapatite (hereinafter termed coated porous silicon). One of each specimen type and one control (titanium disc of the same dimensions as the test specimens) were used per animal in the 1, 4, and 12 week study. Two porous silicon samples and two titanium samples were used per animal for the 26 week study.

The 1, 4, and 12 week trials used a total of 30 guinea pigs (10 guinea pigs for each time period). The 26 week trial used a further 5 guinea pigs, making a total of 35 guinea pigs. There was a pilot phase of the trial for seven days prior to the 1, 4, 12, and 26 week periods. The pilot study was carried out on three guinea pigs (one from each of the 1, 4, and 12 week groups). The pilot study was successful (ie no gross reactions to the implants occurred) so the full scale study proceeded as planned.

Animals were acclimatised to the Experimental Animal House (EAH) environment for at least 5 days prior to experimentation. Following this period each animal was implanted with a transponder (Biomedic Data Systems) for identification and to enable body temperature to be monitored throughout the procedure. The transponder was implanted subcutaneously via a 12 gauge needle in the dorsal region, at a site where it did not interfere with the subsequent implantation of silicon or control specimens. The area of injection was shaved and a local anaesthetic used.

4-7 days later animals were given a general anaesthetic (Halothane 1.5-2.5%) and 4 test specimens implanted. The back of the animal was shaved and an incision of the skin made. Subcutaneous pockets were made by blunt dissection, with the base of the pocket at least 15 mm from the line of the incision. One implant was placed in each pocket, and the implants were at least 5 mm from each other. Four pockets were made to allow placement of 4 implants. The incision was closed by use of appropriate suture material.

Body temperature (via the transponder) was measured twice a day following surgery for the duration of the study (including the seven day pilot study). Each of the implant sites was closely examined and the extent of any reaction noted. The diameter of each implant site was measured to assess swelling and any reddening scored (0=normal, no different from surround skin; 1=some light red coloration in patches; 2=uniform light red coloration or patches of darker red; 3 darker red over all of implant site). At the end of the relevant study period (1, 4, 12 or 26 weeks) animals were killed by an overdose of pentobarbitone. The implant sites were carefully inspected and standard tissue sections of each site were submitted, stained with haematoxylin and eosin and evaluated for various pathological features using a Zeiss Axioplan Photomicroscope. A range of pathological features reflecting the tissue response including acute inflammation and fibrosis were graded by assigning a numerical score to each feature; by comparing score grades with respect to time and implant site, an objective comparison of the silicon materials was obtained. The criteria used in assigning score grades for each pathological feature assessed are summarised in Tables A to D. The specimen type at each implant site was randomised and the experiments and evaluation conducted blind. The scores or values for each specimen type and each time point were compared with those of the control specimens using appropriate non-parametric tests. Multi-factorial analysis of variance was used where possible, with ad hoc tests for differences between groups.

Mean temperature and weight data is shown in graphical form are shown in FIGS. 7 and 8 respectively. There was a significant rise in temperature (FIG. 9) and a significant decrease in weight gain (FIG. 10) for the 7 day period following surgery in all 3 groups of animals (1,4 and 12 weeks). No analogous changes were observed in the 26 week group of animals. Thereafter a steady decline in body temperature and a steady increase in weight was apparent, indicating that no chronic inflammatory reaction to the implants has occurred.

The transient effects on temperature and weight gain are due to the surgical procedure and unrelated to the nature of the implants.

At the time of performing the histological appraisal, the allocation of test and control sites for each experimental animal was unknown and the histological examination was performed blind. Following appraisal, the results were decoded: a summary of the score grades for each implant type with respect to animal number, histological feature and time-point are summarised in the tables E to H. In general the autopsy examination revealed no evidence of any significant pathological change at any of the three time-points. In particular, all implants were easily extracted from their respective implantation sites and showed no evidence of fibrotic tethering to the surrounding connective tissues. At the earliest time-point each site showed obvious acute inflammation associated with mild to moderate neo-vascularization. At 26 weeks, three out of the twenty sites examined showed mild to moderate chronic inflammation/fibrosis around the vicinity of the implantation site consisting of a cuff of macrophages, lymphocytes and occasional foreign body giant cells. In each case these changes were almost exclusively limited to the implantation site. The histological findings were entirely consistent with the features noted at autopsy. The scores for each of the four classes of pathology (Tables E to H) were compared with respect to time (ie week 1 vs. week 4 vs. week 12 vs week 26) and implant type (the scores of each silicon type compared with the titanium control). Details of the statistical analysis are shown at Tables I and J.

Acute inflammation at week 1 was significantly greater than at weeks 4 and 12 but no difference was found between weeks 4, 12, and 26 (Table I).

Tissue degeneration was significantly higher at weeks 1 and 4 when compared to week 12, with no difference between weeks 1 and 4. There was no significant difference in tissue degeneration/necrosis between test and control samples in any of the weeks. New vessel/granulation tissue formation was significantly higher at weeks 1 and 4 than at weeks 12 and 26; there was no significant difference between weeks 1 and 4. Chronic inflammation was significantly higher at week 4 than at weeks 1, 12 and 26; and it was significantly higher at week 12 than week 1. In general, these significant findings were consistent with the three distinct patterns of pathological change observed at the three excision time-points, summarised below.

All sites at one week post-implantation showed features that reflected the immediate response to the injury induced by the surgical procedures to implant the materials. Most sites showed moderate acute inflammation with infiltration of the tissues at the implantation site by neutrophils and macrophages. These changes were associated at the majority sites with oedema of the connective tissues, focal haemorrhage and necrosis and early invasion of the margins of the implant site by proliferating capillary loops. At no site did these changes extend beyond the margins of the implant and into the surrounding skin above or skeletal muscle below.

Although a very few sites showed persistent, low grade acute inflammation four weeks post-implantation, the majority of sites showed features that were consistent with the progression of the features described at one week and represented attempts at tissue repair following surgery rather than a reaction to the silicon implant. Most sites showed areas haemorrhage surrounded by loose granulation tissue, active proliferation of new blood vessels and a limited population of active fibroblasts. In a few cases these reparative features extended beyond the implantation site but, even in these cases, did not cause major disruption to the surrounding tissue architecture.

By twelve weeks, the histological features represented a maturation of the granulation (repair) tissue response observed at four weeks. Although many of the implantation sites still showed significant infiltration by macrophages, lymphocytes and occasional fibroblasts, they showed no evidence of significant fibrotic scarring and a definite reduction in vascular proliferation. Furthermore, in no case did the persistent pathological change extend beyond the implantation site.

In general after 26 weeks, the implantation sites all showed little evidence of any significant tissue reaction to either the test or standard implants. The sites displaying mild to moderate chronic inflammation around the immediate vicinity of the implantation site consisted of a cuff of macrophages, lymphocytes and occasional foreign body giant cells which did not involve the continuous soft and connective tissues and were not associated with distorting fibrosis of nearby structures.

The major internal organs were also examined at autopsy after 26 weeks implantation, with representative blocks being submitted for routine histopathological examination. In keeping with the observations made at the time of autopsy, histological examination of the major internal organs revealed no evidence of any pathology that could be ascribed to the silicon or titanium implants or any pre-existing disease in the experimental population.

The post-evaluation analysis of the scores for each implant type revealed a significantly higher level of chronic inflammation/fibrosis at weeks 4 and 12 for the porous silicon (uncoated) specimens when compared to the titanium controls (Table J). The nature of the tissue reaction noted is likely to be a reflection of the bioactive nature of the porous silicon implant type, suggesting that this material encourages tissue growth and interacts with biological systems. No other statistically significant differences were revealed for the other histological features or implant types at any of the time points.

The results of this study clearly demonstrate that there has been little or no reaction either the test or standard implant materials. The significant differences in histological features reflect changes which would be expected from any surgical procedure and are unrelated to the nature of the implant materials.

The significant differences in the chronic inflammation scores for the porous silicon at weeks 4 and 12 highlighted by the multivariant analysis are unlikely to be biologically significant in terms of biocompatability. This conclusion is confirmed by the results of the 26 week study.

Score Grades

Tables A to D indicate the score grade criteria that were used to assess acute inflammatory reaction; tissue degeneration, oedema formation, haemorrhage and skin necrosis; new vessel and granulation tissue formation; and persistent (chronic) inflammation and tissue fibrosis during pathology.

Tables E to H show the pathology score grades for 1, 4, 12, and 26 weeks after implantation, respectively.

Table I shows a statistical analysis of the biocompatibility study. For table I average rank of scores for each histology category for each time period. In table I a line between two rows in the significance column indicates a significant difference for those two groups (p<0.05; Kruskall-Wallis analysis).

Table J shows statistical analysis of the biocompatibility study. For table J average rank of scores for each implant type by histology category for each time period. In table J "*"

denotes a significant difference between the rank for that silicon type in comparison to the titanium control ($p<0.05$; Friedman analysis), where BSi=Bulk silicon, PSi=Porous silicon, CoPSi=Coated porous silicon.

Figure 10:
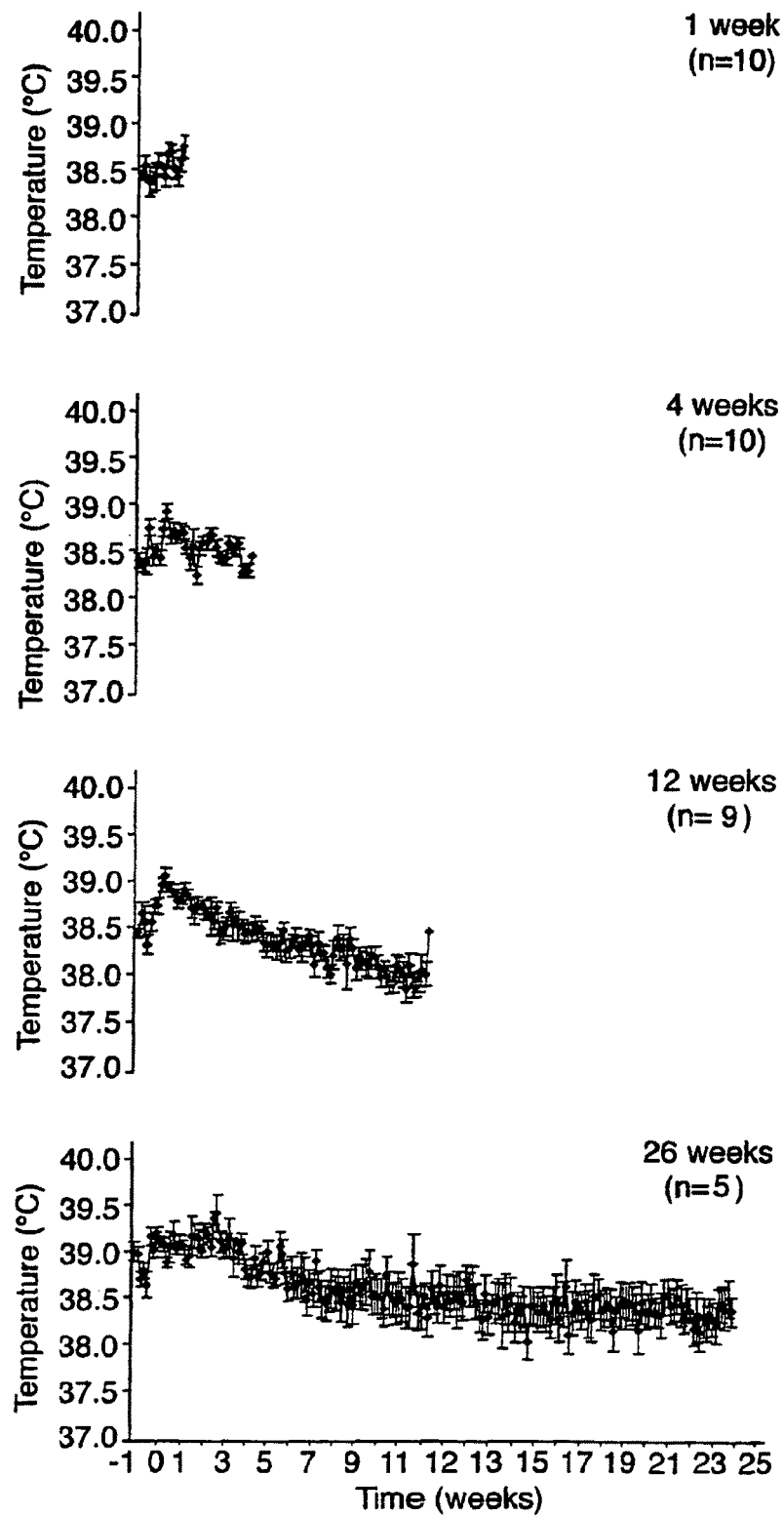
FIG. 10 shows the mean (+/−sem) daily temperature for each of the four groups of guinea pigs.
Figure 11:
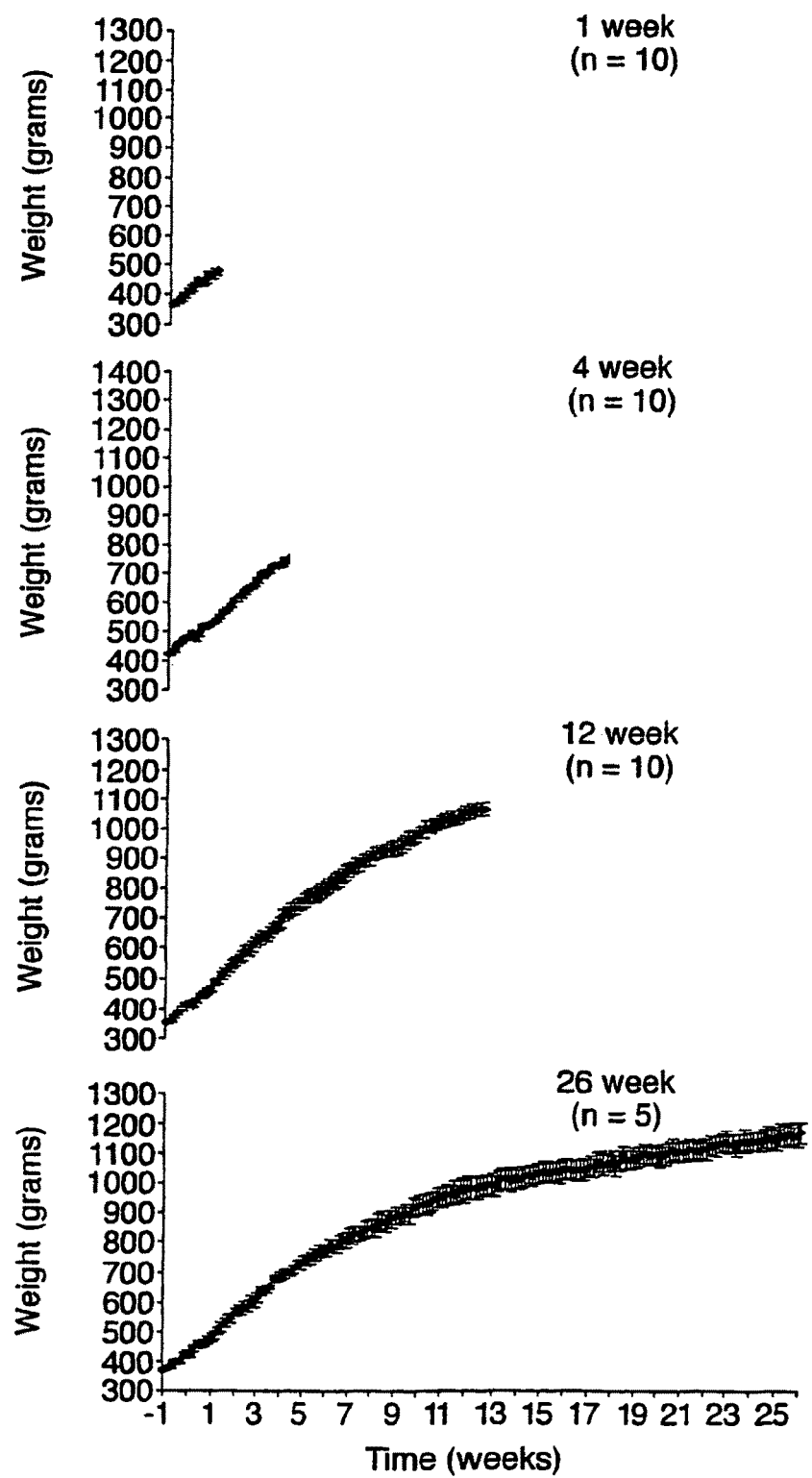
FIG. 11 shows mean (+/−sem) daily weight for each of the four groups of guinea pigs.
Figure 12:
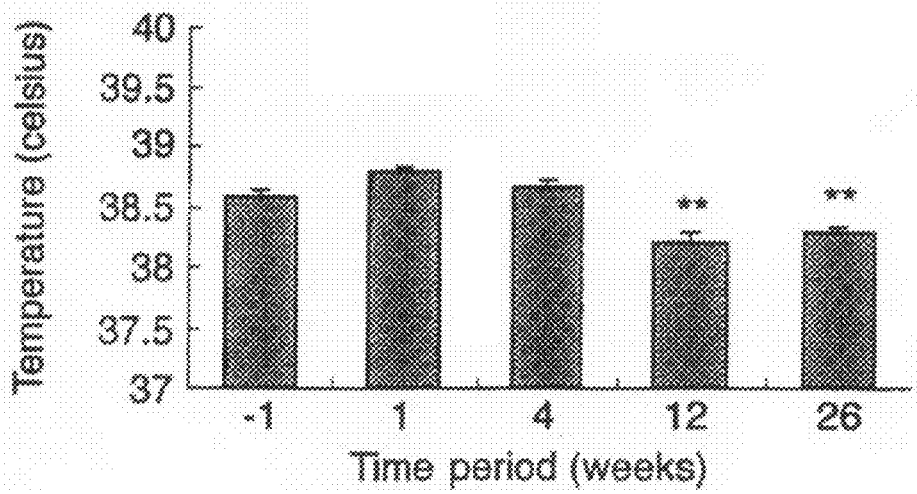
FIG. 12 shows a comparison of guinea pig mean (+sem) temperature for the 7 day control period and for the subsequent 1, 4, 12, and 26 week periods.
Figure 13:
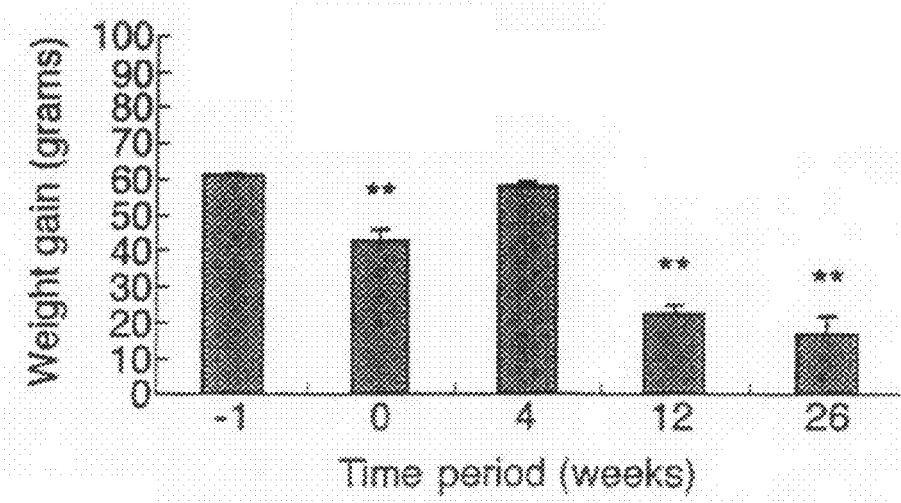
FIG. 13 shows a comparison of guinea pig mean (+sem) weight gain for the 7 day control period and for the subsequent 1, 4, 12, and 26 week periods.

FIGS. 10 to 13 show the physiological parameters from the biocompatibility study. FIG. 10 shows the mean (+/−sem) daily temperature for each of the four groups of guinea pigs. FIG. 11 shows mean (+/−sem) daily weight for each of the four groups of guinea pigs. FIG. 12 shows a comparison of guinea pig mean (+sem) temperature for the 7 day control period prior to surgery (week −1, n=30) with the 4 time periods prior to culling each group of animals (week 1, n=35; week 4, n=24[1]; week 12, n=14[1]; week 26, n=5). The double asterisk "" shown in FIG. 12 indicates $p<0.01$ in comparison to control period. The temperature transponder of 1 animal malfunctioned; data for this animal is therefore missing. FIG. 13 shows a comparison of guinea pig mean (+sem) weight gain for the 7 day control period prior to surgery (week −1, n=30) with the 4 time periods prior to culling each group of animals (week 1, n=35; week 4, n=25; week 12, n=15; week 26, n=5). The double asterisk "" shown in FIG. 13 indicates $p<0.01$ in comparison to control period.

TABLE A

| Grade | Description of Histological Features |
|---|---|
| 0. | No histological evidence of any acute inflammatory reaction. |
| 1. | Small discrete clusters of inflammatory cells consisting predominantly of neutrophils and activated macrophages with occasional eosinophils and lymphocytes. |
| 2. | Continuous sheets of acute inflammatory cells showing invasion of connective tissues in the immediate vicinity of the implanted material. |
| 3. | Similar features to 2. above but associated with either necrosis of connective tissues and/or extension of cellular infiltrate beyond the vicinity of the implant. |

TABLE B

| Grade | Description of Histological Features. |
|---|---|
| 0. | No histological evidence of oedema, haemorrhage or tissue necrosis. |
| 1. | Mild oedema of the connective tissues in the immediate vicinity of the implant. |
| 2. | Significant oedema associated with either haemorrhage and/or necrosis in the vicinity of the implant. |
| 3. | Similar features to 2. above but extending beyond the implant and involving adjacent connective tissues and muscle. |

TABLE C

| Grade | Description of Histological Features |
|---|---|
| 0. | No histological evidence of new vessel formation. |
| 1. | Focal formation of isolated capillary loops in regions of tissue haemorrhage and/or necrosis. |
| 2. | Continuous sheets of new vessel formation in association with local accumulations of fibroblasts to form loose granulation tissue limited to the vicinity of the implant. |
| 3. | Similar features to 2. above but extending beyond the implant and involving adjacent connective tissues and muscle. |

TABLE D

| Grade | Description of Histological Features |
|---|---|
| 0. | No histological evidence of either persistent (chronic) inflammation or early deposition of collagen (fibrosis). |
| 1. | Small discrete foci of macrophages and lymphocytes which may or may not be associated with small populations of fibroblasts and new collagen deposition. |
| 2. | Obvious sheets of chronic inflammatory cells and/or discrete granulomata associated with fibrous scar tissue in the vicinity of the implant. |
| 3. | Similar features to 2. above but extending beyond the implant and involving adjacent connective tissues and muscle. |

TABLE E

| | | Score Grade. | | | | | | | | | | | | | | | |
|---|---|---|---|---|---|---|---|---|---|---|---|---|---|---|---|---|---|
| | | Inflammation | | | | Tissue Degeneration/Necrosis. | | | | New Vessels/ Granulation Tissue. | | | | Chronic Inflammation/Fibrosis. | | | |
| Group. | Animal No. | TI | BSI | PSI | CoPSI | TI | BSI | PSI | CoPSI | TI | BSI | PSI | CoPSI | TI | BSI | PSI | CoPSI |
| +7 Days. | Si/GG/001. | 1 | 1 | 1 | 2 | 0 | 0 | 0 | 1 | 1 | 1 | 1 | 2 | 0 | 0 | 0 | 0 |
| +7 Days. | Si/GG/002. | 2 | 1 | 1 | 1 | 1 | 0 | 0 | 0 | 2 | 1 | 1 | 1 | 0 | 0 | 0 | 0 |
| +7 Days. | Si/GG/003. | 1 | 1 | 1 | 0 | 0 | 1 | 0 | 0 | 1 | 2 | 1 | 1 | 0 | 0 | 0 | 0 |
| +7 Days. | Si/GG/004. | 1 | 1 | 2 | 1 | 0 | 0 | 1 | 0 | 1 | 1 | 2 | 1 | 0 | 0 | 0 | 0 |
| +7 Days. | Si/GG/005. | 1 | 2 | 2 | 2 | 0 | 1 | 1 | 1 | 1 | 2 | 2 | 1 | 0 | 0 | 0 | 0 |
| +7 Days. | Si/GG/006. | 1 | 1 | 2 | 1 | 0 | 0 | 1 | 0 | 1 | 1 | 1 | 1 | 0 | 0 | 0 | 0 |
| +7 Days. | Si/GG/007. | 1 | 1 | 1 | 1 | 0 | 0 | 0 | 0 | 1 | 1 | 1 | 2 | 0 | 0 | 0 | 0 |
| +7 Days. | Si/GG/008. | 1 | 1 | 1 | 1 | 1 | 0 | 0 | 0 | 1 | 1 | 1 | 1 | 0 | 0 | 0 | 0 |
| +7 Days. | Si/GG/009. | 1 | 1 | 1 | 1 | 0 | 0 | 0 | 0 | 1 | 1 | 1 | 1 | 0 | 0 | 0 | 0 |
| +7 Days. | Si/GG/010. | 1 | 1 | 1 | 1 | 0 | 0 | 0 | 0 | 2 | 1 | 1 | 1 | 0 | 0 | 0 | 0 |

Ti Titanium control

BSi Bulk Silicon

PSI Porous Silicon

CoPSi Porous Silicon Coated with hydroxyapatite

TABLE F

| Group | Animal No. | Inflammation | | | | Tissue Degeneration/Necrosis | | | | New Vessels/Granulation Tissue | | | | Chronic Inflammation/Fibrosis | | | |
|---|---|---|---|---|---|---|---|---|---|---|---|---|---|---|---|---|---|
| | | TI | BSI | PSI | CoPSI | TI | BSI | PSI | CoPSI | TI | BSI | PSI | CoPSI | TI | BSI | PSI | CoPSI |
| +4 Weeks. | Si/GG/011. | 0 | 0 | 0 | 0 | 0 | 0 | 0 | 0 | 0 | 1 | 1 | 1 | 0 | 2 | 2 | 2 |
| +4 Weeks. | Si/GG/012. | 0 | 0 | 0 | 0 | 0 | 0 | 0 | 1 | 1 | 1 | 1 | 0 | 1 | 2 | 2 | 1 |
| +4 Weeks. | Si/GG/013. | 0 | 0 | 1 | 0 | 0 | 0 | 0 | 1 | 0 | 1 | 1 | 1 | 1 | 2 | 3 | 2 |
| +4 Weeks. | Si/GG/014. | 0 | 0 | 0 | 0 | 0 | 0 | 0 | 1 | 1 | 0 | 1 | 1 | 1 | 2 | 2 | 3 |
| +4 Weeks. | Si/GG/015. | 0 | 0 | 0 | 0 | 0 | 0 | 0 | 0 | 0 | 1 | 0 | 1 | 1 | 1 | 1 | 1 |
| +4 Weeks. | Si/GG/016. | 0 | 0 | 1 | 0 | 0 | 0 | 1 | 0 | 1 | 1 | 2 | 1 | 2 | 2 | 3 | 2 |
| +4 Weeks. | Si/GG/017. | 0 | 0 | 0 | 0 | 0 | 0 | 1 | 0 | 1 | 1 | 1 | 1 | 2 | 2 | 2 | 1 |
| +4 Weeks. | Si/GG/018. | 0 | 0 | 0 | 0 | 0 | 1 | 0 | 1 | 1 | 1 | 0 | 1 | 2 | 1 | 2 | 1 |
| +4 Weeks. | Si/GG/019. | 0 | 0 | 0 | 0 | 0 | 0 | 0 | 1 | 1 | 1 | 1 | 0 | 1 | 2 | 1 | 1 |
| +4 Weeks. | Si/GG/020. | 0 | 0 | 0 | 0 | 0 | 0 | 0 | 0 | 0 | 1 | 1 | 0 | 0 | 1 | 2 | 1 |

Ti Titanium control
BSi Bulk Silicon
PSi Porous Silicon
CoPSI Porous Silicon Coated with hydroxyapatite

TABLE G

| Group | Animal No. | Inflammation | | | | Tissue Degeneration/Necrosis | | | | New Vessels/Granulation Tissue | | | | Chronic Inflammation/Fibrosis | | | |
|---|---|---|---|---|---|---|---|---|---|---|---|---|---|---|---|---|---|
| | | TI | BSI | PSI | CoPSI | TI | BSI | PSI | CoPSI | TI | BSI | PSI | CoPSI | TI | BSI | PSI | CoPSI |
| +12 Weeks | Si/GG/021. | | | 0 | 0 | | | 0 | 0 | | | 1 | 0 | | | 2 | 0 |
| +12 Weeks | Si/GG/022. | 0 | 0 | 0 | 0 | 0 | 0 | 0 | 0 | 0 | 0 | 0 | 0 | 1 | 0 | 0 | 0 |
| +12 Weeks | Si/GG/023. | 0 | 0 | 0 | 0 | 0 | 0 | 0 | 0 | 0 | 0 | 0 | 0 | 0 | 1 | 1 | 2 |
| +12 Weeks | Si/GG/024. | 0 | 0 | 0 | 0 | 0 | 0 | 1 | 0 | 0 | 0 | 1 | 0 | 0 | 0 | 2 | 0 |
| +12 Weeks | Si/GG/025. | 0 | 0 | 0 | 0 | 0 | 0 | 0 | 0 | 0 | 1 | 0 | 0 | 0 | 1 | 0 | 1 |
| +12 Weeks | Si/GG/026. | 0 | 0 | | | 0 | 0 | | | 0 | 0 | | | 0 | 0 | | |
| +12 Weeks | Si/GG/027. | 0 | 0 | | 0 | 0 | 0 | | 0 | 0 | 0 | | 0 | 0 | 0 | 2 | 0 |
| +12 Weeks | Si/GG/028. | 0 | 0 | 0 | 0 | 0 | 0 | 0 | 0 | 1 | 0 | 1 | 0 | 1 | 0 | 1 | 0 |
| +12 Weeks | Si/GG/029. | 0 | 0 | 0 | 0 | 0 | 0 | 0 | 0 | 0 | 0 | 0 | 1 | 0 | 0 | 2 | 2 |
| +12 Weeks | Si/GG/030. | 0 | 0 | 0 | 0 | 0 | 0 | 0 | 0 | 0 | 0 | 1 | 0 | 0 | 0 | 2 | 0 |

Ti Titanium control
BSi Bulk Silicon
PSi Porous Silicon
CoPSI Porous Silicon Coated with hydroxyapatite

TABLE H

| Group | Animal No. | Inflammation | | | | Tissue Degeneration/Necrosis | | | | New Vessels/Granulation Tissue | | | | Chronic Inflammation/Fibrosis | | | |
|---|---|---|---|---|---|---|---|---|---|---|---|---|---|---|---|---|---|
| | | TI | TI | PSI | PSI | TI | TI | PSI | PSI | TI | TI | PSI | PSI | TI | TI | PSI | PSI |
| +26 weeks. | Si/GG/031. | 0 | 0 | 0 | 0 | 0 | 0 | 0 | 0 | 0 | 0 | 0 | 0 | 0 | 0 | 0 | 0 |
| +26 weeks. | Si/GG/032. | 0 | | 0 | | 0 | | 0 | | 0 | | 0 | | 0 | | 0 | |
| +26 weeks. | Si/GG/033. | 0 | 0 | 0 | 0 | 0 | 0 | 0 | 0 | 0 | 0 | 0 | 0 | 0 | 0 | 2 | 0 |
| +26 weeks. | Si/GG/034. | 0 | 0 | 0 | 0 | 0 | 0 | 0 | 0 | 0 | 0 | 0 | 0 | 0 | 0 | 0 | 1 |
| +26 weeks. | Si/GG/035. | 0 | 0 | 0 | 0 | 0 | 0 | 0 | 0 | 0 | 0 | 0 | 0 | 0 | 0 | 2 | 0 |
| +26 weeks. | Si/GG/036. | N/A. | N/A. | N/A. | N/A. | N/A. | N/A. | N/A. | N/A. | N/A. | N/A. | N/A. | N/A. | N/A. | N/A. | N/A. | N/A. |

Ti Titanium control
PSi Porous Silicon
N/A: Not applicable, control (non-implanted animal).

TABLE I

| Group | Inflammation | | Tissue Degeneration/Necrosis | | New vessels/ Granulation Tissue | | Chronic Inflammation/Fibrosis | |
|---|---|---|---|---|---|---|---|---|
| | Average rank | Significance | Average rank | Significance | Average rank | Significance | Average rank | Significance |
| Week 1 | 112.5 | > | 73.6 | > | 99.2 | > > > | 40.0 | > > > |
| Week 4 | 50.2 | | 71.9 | | 76.8 | | 104.4 | |
| Week 12 | 47.0 | | 60.4 | | 41.2 | | 65.1 | |
| Week 26 | 47.0 | | 58.5 | | 29.0 | | 51.5 | |

TABLE J

| | | Average Rank | | | |
|---|---|---|---|---|---|
| Group | Implant Type | Inflammation | Tissue Degeneration | New Vessels/ Granulation | Chronic Inflammation/Fibrosis |
| Week 1 | Titanium | 2.4 | 2.45 | 2.5 | 2.5 |
| | BSi | 2.4 | 2.45 | 2.5 | 2.5 |
| | PSi | 2.8 | 2.65 | 2.5 | 2.5 |
| | CoPSi | 2.4 | 2.45 | 2.5 | 2.5 |
| Week 4 | Titanium | 2.4 | 2.1 | 2.15 | 1.85 |
| | BSi | 2.4 | 2.3 | 2.75 | 2.70 |
| | PSi | 2.8 | 2.5 | 2.75 | 3.20* |
| | CoPSi | 2.4 | 3.1 | 2.35 | 2.25 |
| Week 12 | Titanium | 2.5 | 2.44 | 2.33 | 2.11 |
| | BSi | 2.5 | 2.44 | 2.33 | 2.11 |
| | PSi | 2.5 | 2.67 | 3.00 | 3.33* |
| | CoPSi | 2.5 | 2.44 | 2.33 | 2.44 |
| Week 26 | Titanium | 1.5 | 1.5 | 1.5 | 1.33 |
| | PSi | 1.5 | 1.5 | 1.5 | 1.67 |

The invention claimed is:

1. A device comprising:
   a) a mesoporous resorbable or bio-erodible anodized carrier material having a silica or silicon oxide surface,
   b) a beneficial substance associated with the carrier, wherein the beneficial substance is not an element or a salt of a metal.

2. A device according to claim 1, wherein the silica or silicon oxide surface completely covers the carrier material.

3. A device according to claim 1, wherein the beneficial substance is present in the pores of the carrier material.

4. A device according to claim 1, wherein the carrier material has a porosity of between 2% and 80%.

5. A device according to claim 1, wherein the beneficial substance is a drug selected from an organic molecule, protein, peptide, or gene fragment or other DNA material.

6. A device according to claim 1, further comprising at least one additional beneficial substance associated with the carrier.

7. A device according to claim 1, wherein the carrier material delivers an effective amount of the beneficial substance for a period of between a month and one year.

8. A device according to claim 1, wherein the carrier material is associated with between 10 micrograms and 5 milligrams of the beneficial substance.

9. A method of administering a beneficial substance to a mammal in need thereof, comprising administering the device of claim 1 to the mammal.

10. A method according to claim 9, wherein the carrier material has a porosity of between 2% and 80%.

11. A method according to claim 9, wherein the beneficial substance is a drug selected from an organic molecule, protein, peptide, or gene fragment or other DNA material.

12. A method according to claim 9, comprising delivering an effective amount of the beneficial substance for a period of between a month and one year.

13. A method according to claim 9, whereby between 10 micrograms and 5 milligrams of the beneficial substance are administered.

14. A method according to claim 9, whereby the beneficial substance is delivered to a specific site of the mammal.

15. A method according to claim 14, wherein the specific site is an organ of the mammal.

16. A method according to claim 9, wherein the carrier material further comprises at least one additional beneficial substance associated with the carrier material.

17. A method according to claim 9, comprising injecting the carrier material into a specific site of the mammal.

18. A method according to claim 17, wherein the specific site is an organ of the mammal.

19. A method according to claim 9, whereby the beneficial substance is present in the blood of the mammal at a level of about 1 to 10 micrograms per liter.

20. A device comprising:
   a) a mesoporous resorbable or bio-erodible anodized carrier material having a silica or silicon oxide surface, and
   b) a beneficial substance disposed in pores of the carrier material.

21. A device according to claim 20, wherein the silica or silicon oxide surface completely covers the carrier material.

22. A device according to claim 20, wherein the carrier material is porous substantially throughout its volume.

23. A device according to claim 20, wherein the carrier material has a porosity of between 2% and 80%.

24. A device according to claim 20, wherein the beneficial substance is a drug selected from an organic molecule, protein, peptide, or gene fragment or other DNA material.

25. A device according to claim 20, further comprising at least one additional beneficial substance associated with the carrier.

26. A device according to claim 20, wherein the carrier material delivers an effective amount of the beneficial substance for a period of between a month and one year.

27. A device according to claim 1, wherein the carrier material is associated with between tens of micrograms and a few milligrams of the beneficial substance.

28. A device according to claim 1, wherein the device has a largest dimension x, wherein $0 < x \leqq 2$ mm.

29. A device according to claim 1, which is sized for injection through a needle.

30. A method according to claim 9, wherein the carrier material is associated with between tens of micrograms and a few milligrams of the beneficial substance.

31. A method according to claim 9, wherein the device has a largest dimension x, wherein $0 < x \leqq 2$ mm.

32. A method according to claim 9, wherein the device is sized for injection through a needle.

33. A device according to claim 20, wherein the carrier material is associated with between tens of micrograms and a few milligrams of the beneficial substance.

34. A device according to claim 20, wherein the device has a largest dimension x, wherein $0 < x \leqq 2$ mm.

35. A device according to claim 20, which is sized for injection through a needle.

36. A device according to claim 1, wherein the anodized carrier material was formed by anodization and wet etching.

37. A method according to claim 9, wherein the anodized carrier material was formed by anodization and wet etching.

38. A device according to claim 20, wherein the anodized carrier material was formed by anodization and wet etching.

39. A device according to claim 1, wherein the device has a weight of less than a milligram.

40. A method according to claim 9, wherein the device has a weight of less than a milligram.

41. A device according to claim 20, wherein the device has a weight of less than a milligram.

* * * * *

UNITED STATES PATENT AND TRADEMARK OFFICE
CERTIFICATE OF CORRECTION

PATENT NO. : 8,318,194 B2  
APPLICATION NO. : 12/801825  
DATED : November 27, 2012  
INVENTOR(S) : Canham et al.

Page 1 of 1

It is certified that error appears in the above-identified patent and that said Letters Patent is hereby corrected as shown below:

At column 23, claim number 1, line number 36, please insert --and-- after "oxide surface,".

Signed and Sealed this
Twenty-ninth Day of January, 2013

David J. Kappos
*Director of the United States Patent and Trademark Office*